United States Patent [19]

Sparks et al.

[11] 4,239,714
[45] Dec. 16, 1980

[54] METHOD FOR MODIFYING THE PORE SIZE DISTRIBUTION OF A MICROPOROUS SEPARATION MEDIUM

[75] Inventors: Robert E. Sparks, Kirkwood, Mo.; Mariam M. Wahab, Columbus, Ohio; Norbert S. Mason, Clayton, Mo.

[73] Assignee: Washington University, St. Louis, Mo.

[21] Appl. No.: 960,745

[22] Filed: Nov. 15, 1978

[51] Int. Cl.$^3$ .............................................. B29D 27/00
[52] U.S. Cl. .................................. 264/45.5; 210/500.2; 264/41; 264/129; 264/340; 264/DIG. 13; 264/DIG. 18; 264/321
[58] Field of Search ................. 264/321, 41, 340, 129, 264/45.5, 45.1, DIG. 13, DIG. 18; 210/500 M

[56] References Cited

U.S. PATENT DOCUMENTS

| | | | |
|---|---|---|---|
| 3,519,708 | 7/1970 | McMichael | 264/321 |
| 3,637,415 | 1/1972 | Civardi | 264/321 X |
| 3,709,774 | 1/1973 | Kimura . | |
| 3,718,532 | 2/1973 | Hayes . | |
| 3,755,517 | 8/1973 | Clancy et al. | 264/321 X |
| 3,837,900 | 9/1974 | Englert et al. . | |
| 3,852,388 | 12/1974 | Kimura . | |
| 3,873,665 | 3/1975 | Segovia | 264/321 |
| 4,082,704 | 4/1978 | Rudner et al. | 264/321 X |

*Primary Examiner*—Philip Anderson
*Attorney, Agent, or Firm*—Holman & Stern

[57] ABSTRACT

The pore size distribution of a microporous separation medium, such as a membrane or gel, is modified so as to provide it with a sharp upper cut-off of preselected molecular size. The modification is effected by first filling the pores of the separation medium with a volatile liquid, and then evaporating a controlled amount of the volatile liquid to form voids at the entrances to the pores. A concentrated solution of a cross-linkable or polymerizable pore-blocking agent, such as a protein, enzyme or polymeric material, is then applied to the surface of the separation medium. The pore-blocking agent is a material which is insoluble in the volatile liquid and whose molecular size distribution has a lower limit corresponding to the preselected molecular size, whereby the pore-blocking agent selectively enters only those pores larger than the preselected size and remains in the voids at the entrances to the pores. After removing excess pore-blocking agent solution from the surface of the separation medium, the pore-blocking agent is insolubilized by cross-linking or polymerization so as to immobilize it within the voids and thereby obstruct the entrances to all of the pores larger than the preselected size.

8 Claims, No Drawings

METHOD FOR MODIFYING THE PORE SIZE DISTRIBUTION OF A MICROPOROUS SEPARATION MEDIUM

BACKGROUND OF THE INVENTION

The Government has rights in this invention pursuant to the invention having been made under Grant from the Department of Health, Education and Welfare.

This invention relates to a method of modifying the pore size distribution of microporous separation media so as to provide it with a sharp upper cut-off of preselected molecular size.

In recent years there has been increasing activity in the use of selective microporous separation media, particularly membranes and chromatographic gels, for separations of biologically important materials, including, for example, proteins, enzymes, viruses and immunological active fragments. The various partition system separation techniques employing such separation media, such as ultrafiltration, dialysis, electro-dialysis, electrophoresis, gel permeation chromatography and gel exclusion chromatography, have proven to be much more suitable for separations of labile biological molecules than precipitative or solvent removal separation techniques, due to their relative gentleness and the fact that they do not cause severe denaturation.

The partition system separation techniques all depend upon the membrane or gel particle not accepting molecules above a certain size. Such molecular size limit of the membrane or gel is usually defined in terms of the molecular weight of a spherical uncharged molecule which would just be retained by the membrane or excluded by the gel, and is termed the "cut-off". Due to the randomness of the formation of bonds and cross-links during the generation of the membrane or gel, and the attendant difficulties in obtaining a precise control of the pore size distribution thereof, the membranes and gels presently commercially available do not have a sharply defined cut-off, but rather are designated by a nominal cut-off representing the molecular weight of molecules retained 80–90%. Such diffuseness of the cut-off of the membranes and gels substantially reduces their separation selectivity and efficiency.

SUMMARY OF THE INVENTION

It is, accordingly, a primary object of the present invention to produce a microporous separation media exhibiting improved separation selectivity and efficiency in comparison with those previously available.

Another object of the invention is to produce a microporous separation media in accordance with the preceding object, whose pore size distribution has a sharp upper cut-off of preselected molecular size.

A further object of the invention is to provide a method of modifying the pore size distribution of commercially available microporous separation media so as to provide it with a sharp upper cut-off of preselected molecular size.

Still another object of the invention is to provide a method in accordance with the preceding object, which is relatively simple and economical to perform.

The above and other objects are achieved in accordance with the present invention by means of a method of treating a preformed microporous separation medium so as to effectively block the entrances to all of the pores thereof larger than a preselected molecular size constituting the desired cut-off, but leaving unchanged the smaller pores. The method comprises the steps of first filling the pores of the separation medium with a volatile liquid, and then evaporating a controlled amount of the volatile liquid from the separation medium so as to lower the level of the liquid within the pores to below the bulk surface of the separation medium and thereby form voids at the entrances to the pores. A concentrated solution of a pore-blocking agent is then applied to the bulk surface of the separation medium. Such pore-blocking agent is a material which is insoluble in the volatile liquid and capable of being insolubilized in its solution, for example, by polymerization or cross-linking thereof; and whose molecular size distribution has a lower limit corresponding to the preselected molecular size constituting the desired cut-off. Accordingly, the pore-blocking agent selectively enters only those pores larger than the preselected size and remains in the voids at the entrances to the pores. After removing excess pore-blocking agent solution from the bulk surface of the separation medium, the pore-blocking agent is insolublized, for example, by polymerization or cross-linking thereof, so as to immobilize it within the voids and thereby obstruct the entrances to all of the pores larger than the preselected size.

The method in accordance with the present invention results in a modification of the pore size distribution of the microporous separation medium so as to provide it with a sharp upper cut-off of the preselected molecular size. Such modification effectively improves the separation selectivity and efficiency of the separation medium, and transforms it from a gross-separation tool to a fractionation tool capable of effecting sharp molecular separations.

DESCRIPTION OF PREFERRED EMBODIMENTS

The method in accordance with the present invention may be utilized for modifying the pore size distribution of any of a wide variety of microporous separation media in the form of polymeric membranes, chromatographic gels, adsorbents, and the like. Such separation media may be prepared by techniques known in the art, and are generally commercially available in a wide range of pore size distributions from several sources. For example, microporous polymeric membranes suitable as starting materials in the method of the present invention are manufactured and sold by Amicon Corporation, Abcor, Inc., Millipore Corporation, and Nuclepore Corporation, and may be formed from various polymeric materials, including cellulose acetate, cellulose nitrate, polycarbonates, polyolefins, polyacrylics, and polysulfones. Other microporous separation media suitable for use as starting materials in the method of the present invention include chromatographic gels, e.g., the cross-linked dextrans manufactured and sold by Pharmacia Fine Chemicals, Inc. under the trademark "Sephadex", and porous silica gel; and adsorbents, e.g., activated carbon.

The present invention resides in modifying the pore size distribution of such microporous separation media so as to provide it with a sharp upper cut-off of preselected molecular size, by blocking the entrances to those pores larger than such preselected size, but leaving unchanged the smaller pores. The molecule chosen as the pore-blocking agent must be of such size that it would readily enter the pores larger than the preselected size, but could not enter the smaller pores. The pore-blocking agent thus must be a material whose molecular size distribution has a lower limit corresponding to the preselected molecular size, and preferably is a material which is substantially monodisperse, i.e., whose molecular size is substantially uniform and homogeneous. Additionally, the pore-blocking agent must be a material which, after selectively entering those pores larger than the preselected size, is capable of being insolubilized and immobilized within the pores so as to effectively block such pores. A number of polymerizable or cross-linkable materials, including proteins, enzymes, cells, viruses, bacteria, and polymeric materials, have such capability.

Proteins and enzymes are particularly suitable as pore-blocking agents in accordance with the present invention, since they are substantially monodisperse materials available in a wide range of known molecular weights, and are readily cross-linkable, for example, by heat or pH change or by means of several cross-linking agents, such as glutaraldehyde and polylycine. Depending upon the particular preselected molecular size desired for the cutoff, a suitable protein or enzyme whose molecular weight corresponds to such preselected molecular size could be selected as the pore-blocking agent. A representative list of the various proteins and enzymes which could be used as pore-blocking agents, along with their molecular weights, are set forth in Table I, below.

TABLE I

| PROTEIN AND ENZYME PORE-BLOCKING AGENTS | |
|---|---|
| Protein or Enzyme | Molecular Weight |
| Protamine Nucleate | 4,000 |
| Parathormone | 8,000 |
| Cytochrome C | 13,000 |
| Ribonuclease | 13,683 |
| Lysozyme | 14,000 |
| Myoglobin | 17,800 |
| Trypsin | 23,800 |
| α-chymotripsin | 24,500 |
| Chymotrypsinogen | 25,000 |
| Penicillinase | 30,000–36,000 |
| β-lactalbumin | 35,000 |
| Ovalbumin | 40,000 |
| α-amylase | 50,000 |
| Glucoamylase | 50,000 |
| Bovine Serum Albumin | 70,000 |
| Proteolytic enzymes from organisms | 100,000 |
| Transferrin | 100,000 |
| 7-S Globulin | 100,000 |
| Aldolase | 142,000 |
| Immunoglobulins | 160,000 |
| Apoferritin | 300,000 |
| Fibrinogen | 340,000 |
| Acetyl Co-A Carboxylase | 400,000 |
| β-galactosidase | 850,000 |
| Macroglobulins | 860,000 |
| Smallest pathogenic viruses | 2,400,000 |

A wide variety of polymeric materials can also be employed as pore-blocking agents in accordance with the present invention, assuming that they have a sharp lower cut-off to their molecular size distributions. Examples of such polymeric materials (along with suitable cross-linking or polymerizing agents and conditions therefor) include the following: polyvinylpyrrolidone (ammonium persulfate, thirty minutes in water at 90° C.; diazo compounds plus ultraviolet light; oxidizing agents such as dichromate plus ultraviolet light); polyvinyl alcohol (dimethylol urea; trimethylol melamine; dimethylolethylene urea; dialdehydes; polyvalent metals; 10% glyoxal based on PVA; organic titanates; succinyl chloride; dianhydrides, such as 3,3',4,4'-benzophenone tetracarboxylic acid dianhydride); methyl cellulose or hydroxypropyl methyl cellulose (dialdehydes; polyphenolic compounds, e.g., tannic acid, urea-formaldehyde and melamine-formaldehyde resins; succinyl chloride); unsaturated polyesters, e.g., maleic or fumaric co-glycol (MEK peroxide); and acryloyl chloride-methyl methacrylate copolymer (10–20% aqueous solution of ethylene diamine, ten minutes at room temperature).

The pore-blocking method in accordance with the present invention is designed to block only the entrances to all of the pores of the separation medium larger than the preselected size, rather than blocking such pores along their entire length. This is so due to the fact that blocking such pores along their entire length would lead to reduced capacity of the separation medium because it would tend to block other pores where these interconnect with the blocked pore.

In order to block the pores only at their entrances, the first step of the procedure is to fill all of the pores of the separation medium with a volatile liquid which is inert with respect to the separation medium and which is a non-solvent for the material to be used as the pore-blocking agent, for example, by soaking the separation medium in the volatile liquid. Suitable volatile liquids may include, for example, alcohols, such as methanol, ethanol, n-propanol, isopropanol, and n-octanol; glycols, such as ethylene or propylene glycol; esters, such as ethyl acetate or propyl acetate; ketones, such as methyl isobutylketone; aromatic hydrocarbons, such as benzene, toluene, xylene; and aliphatic hydrocarbons, such as hexane, heptane and octane. Mixtures of liquids may be used to obtain desired evaporative characteristics, for example, employing a small amount of a volatile liquid mixed with a liquid of low volatility, e.g., a solution of n-propanol in tri-or tetra-ethylene glycol, to achieve a predictable fraction evaporated when the majority of the more volatile liquid has evaporated.

A controlled amount of the volatile liquid is then evaporated from the separation medium so as to lower the level of the liquid within the pores to below the bulk surface of the separation medium and thereby form voids at the entrances to the pores. The period of time for such controlled evaporation will vary depending upon the volatility of the particular volatile liquid employed. With n-propanol, for example, an evaporation period of about thirty seconds will be sufficient. With a liquid of relatively low volatility, application of a vacuum and/or heating may be required to evaporate a sufficient quantity in the desired time.

A relatively concentrated solution of the pore-blocking agent is then applied to the bulk surface of the separation medium, for example, by means of a spray or roller, or by placing the bulk surface of the separation medium on a layer of controlled thickness (e.g., 0.001 to 0.003 inches) of the pore-blocking agent solution. Pressure or electrical potential may also be useful in applying the pore-blocking agent solution. The solvent employed in the pore-blocking agent solution should be inert with respect to the separation medium and may or may not be soluble in the volatile liquid, so long as the interfacial tension between the two liquids is low so that the pore-blocking agent solution will readily penetrate the pores wet with the volatile liquid.

When the pore-blocking agent solution is applied to the bulk surface of the separation medium, the pore-blocking agent molecules will be able to penetrate only those pores of the separation medium which are larger than the lower limit of the molecular size distribution of the pore-blocking agent. By proper selection of the pore-blocking agent so that the lower limit of its molecular size distribution corresponds to the preselected molecular size of the desired cut-off, it is thus possible to ensure that the pore-blocking agent will selectively enter only those pores larger than such preselected size. Furthermore, due to the insolubility of the pore-blocking agent in the volatile liquid, the pore-blocking agent molecules will not penetrate into the pores beyond the level of the volatile liquid within the pores, and thus will remain in the voids formed above such liquid level at the entrances of the pores.

A number of the commercially available microporous separation membranes are known to be asymmetric, i.e., having one side formed with a very tight thin layer which is supported by a much more porous, open structure. Separations employing such membranes are generally carried out with the tight thin layer on the upstream side of the membrane so that the molecules which are retained by the membrane will not penetrate into and accumulate within the membrane. When treating such asymmetric membranes in accordance with the method of the present invention, the pore-blocking agent solution is preferably applied to the tight thin layer of the membrane so that only the oversized pores in such layer need to be blocked.

After allowing sufficient time for the pore-blocking agent to enter the pores, excess pore-blocking agent solution is removed from the bulk surfacce of the separation medium, for example, by gentle physical wiping. Thereafter, the pore-blocking agent is insolubilized, for example, by applying to the bulk surface of the separation medium a polymerization or cross-linking agent for the pore-blocking agent, and allowing the polymerization or cross-linking agent to soak into the pores into contact with the pore-blocking agent. Application of the polymerization or cross-linking agent may be by any suitable means, for example, by spraying or roller coating. The pore-blocking agent is thereby polymerized or cross-linked so as to immobilize it within the voids formed at the entrances to the pores. In this manner, the entrances to all of the pores larger than the preselected molecular size of the desired cut-off, are effectively obstructed. Following insolubilization of the pore-blocking agent, the separation medium is then washed, for example, in running de-ionized water, for a period of time sufficient to remove therefrom all excess amounts of the materials used in the treatment.

The method of the present invention thus enables the production of a whole series of microporous separation media whose pore size distributions may be provided with sharp upper cut-offs tailor-made for effecting any one of numerous important molecular separations including, for example, the fractionation of the various plasma proteins. All that is required is the proper selection of a suitable pore-blocking agent whose molecular size distribution has a lower limit corresponding to the molecular size of the material which is desired to be retained by the separation medium. For example, if it is desired to effect the separation of a specific protein from mixtures thereof with other proteins of smaller molecular size, such specific protein could suitably be used as the pore-blocking agent. This would effectively block all of the pores of the separation medium which are sufficiently large for passage of such specific protein, resulting in retention by the medium of such specific protein, and passage through the medium of the proteins of smaller molecular size.

For large scale production of separation media having a sharp upper cut-off of any given molecular size, the use of a protein or enzyme as the pore-blocking agent for making each individual separation medium would tend to make the media very expensive. A much more economical procedure would be to use the protein or enzyme as the pore-blocking agent only for making a "master" separation medium, analagous to the master phonograph record from which inexpensive copies are made. For example, if it is desired to produce on a large scale microporous membranes having a sharp cut-off at albumin, a master membrane could be made in which albumin was used as the pore-blocking agent. Such master membrane could be used to fractionate a relatively inexpensive polymeric material, whereby the retained polymer will have a lower molecular size limit set by the albumin-blocked master membrane. The retained polymer fraction can then be used as the pore-blocking agent for large scale membrane production, since its lower molecular size limit determines the lower limit of pore sizes blocked. In this manner, relatively inexpensive pore-blocking agents can be generated from master membranes blocked with more exotic and expensive materials.

It is obvious that many other modifications can be employed in the pore-blocking procedure, such as allowing the protein blocking molecule to enter the separation medium at its isoelectric point, where it has the smallest size. If it is then cross-linked at this pH, but used at another, it will act as a somewhat smaller molecule than if the blocking had been carried out at the pH of use. Also, if the blocking is carried out with the separation medium in a state of solvation different from that at which it will be used, then the effective average size of the entire structure can be shifted before or after pore-blocking.

The modification in pore size distribution resulting from the pore-blocking technique of the present invention has been found to substantially improve the separation selectivity and efficiency of the microporous separation medium. The selectivity of a separation medium for a given molecular species may be expressed in terms of its retention for such species, defined as follows:

$$R = 1 - (C_u/C_r) \quad (I)$$

wherein R is the retention of the separation medium for a given molecular species, and $C_u$ and $C_r$ are the instantaneous bulk concentratitons of such species in the ultrafiltrate and retentate, respectively.

The separation efficiency of a separation medium may be expressed in terms of a separation factor for a system of two-molecular species of different molecular size, calculated from the retentions of the separation medium for each molecular species as follows:

$$\alpha 1,2 = (1 - R_1)/(1 - R_2) \quad (II)$$

wherein $\alpha 1,2$ is the separation factor of the separation medium for the two-molecular species system, $R_1$ is the retention of the separation medium for the molecular species of smaller molecular size, and $R_2$ is the retention of the separation medium for the molecular species of larger molecular size. In accordance with the above-defined relationships, a separation factor of 1 represents no separation, and a separation factor of infinity represents complete retention of the molecular species of larger molecular size, with the most desirable situation being where $R_1$ is low and $R_2$ is high.

In evaluating the effect of the pore-blocking technique of the present invention on the performance of a given microporous separation medium in a given system of two-molecular species of different molecular size to be separated, there are two criteria which should be considered. First of all, the criterion for increased separation efficiency is satisified if the pore-blocking modification increases the separation factor of the separation medium. In regard to separation selectivity, it should be noted that the pore-blocking modification should result in an increase in $R_1$ as well as in $R_2$, since when the large pores are blocked, they are blocked for the smaller molecules as well as for the larger ones. The critical parameter in this respect is the ratio of the change in retention of the two-molecular species, i.e., $dR_2/dR_1$. It has been found that if this ratio is greater than the reciprocal of the separation factor of the unmodified separation medium, the criterion for increased selectivity of the modified separation medium is satisified.

The invention is further illustrated by way of the following examples.

EXAMPLE I

An Amicon XM 300 membrane (a microporous polymeric membrane formed from substituted polyolefins) was soaked in n-propanol. The excess was blotted. After a controlled period of evaporation (30 seconds) a 20% by weight solution of gamma globulin (7S) in 0.05 molar NaCl was applied to the active surface by means of a roller coated with a uniform layer of the protein solution. The excess solution was then removed by wiping with a moist cloth twice, and a dry cloth twice. A solution of 25% by weight glutaraldehyde in water was then sprayed on the surface and allowed to soak in for about thirty minutes. This was repeated. The membrane was then washed in running deionized water for sixteen hours.

EXAMPLE II

The following tests were conducted to determine the effect of the pore-blocking procedure described in Example I on the performance of the membrane in effecting a separation of gamma globulin (7S) (molecular weight 100,000) from a mixture thereof with bovine serum albumin (molecular weight 70,000). The tests were carried out in an Amicon No. 52 magnetically stirred cell which had a volume of 65 ml and an effective membrane area of 12.5 cm². A total of 8 Amicon XM 300 membranes were employed, showing no more than 15% variability in water ultrafiltration rates. Separate 0.1 gm % solutions of bovine serum albumin and gamma globulin (7S) were employed as the test species. Feed pressure was provided by nitrogen regulated at 8 psig. In each ultrafiltration run, 40 ml of feed was placed in the ultrafiltration unit and the flux was calculated from the time required to ultrafilter 17.5 ml. To reduce the effect of sorbed proteins on subsequent ultrafiltrations, the membrane was treated after each ultrafiltration with a 0.1% solution of protease from bacillus subtilus for eighteen hours at room temperature. The membrane was then washed free of the enzyme.

The test scheme involved testing the membranes, both before and after the pore modification procedure described in Example I, in ultrafiltrations with each of the two test species in each sequential order. Specifically, a first set of four unmodified membranes were tested first with bovine serum albumin and then with gamma globulin (7S), and a second set of four unmodified membranes were tested with the two test species in reverse order. Then each of the 8 membranes were subjected to the pore modification procedure described in Example I. Thereafter, two membranes from each of the two sets were tested first with bovine serum albumin and then with gamma globulin (7S), and the other two membranes from each of the two sets were tested with the two test species in the reverse order.

Concentrations of the test proteins in the ultrafiltrate and in the retentate were determined either by direct ultraviolet spectrophotometry at 280 nm, or by the Folin-Ciocalteu colorimetric method (Penhost et al, Biochem., Vol. 6, No. 9, p. 2940, 1967). The retention of each protein and the separation factor for the system were calculated from equations (I) and (II) set forth above. The test results are set forth in Table II, below.

TABLE II

| Membrane | Water | Range of Ultrafiltration Rates ml/cm² min atm Bovine Serum Albumin (0.1%) | Gamma Globulin (7S) (0.1%) | Retention ($R_1$) Bovine Serum Albumin | ($R_2$) Gamma Globulin (7S) | Separation Factor ($\alpha_{1,2}$) |
|---|---|---|---|---|---|---|
| Unmodified | 1.5 to 1.8 | 0.26 to 0.96 | 0.14 to 0.28 | 0.09 ±0.02 | 0.54 ±0.04 | 2.0 ±0.2 |
| Modified | | 0.14 to 0.80 | 0.10 to 0.16 | 0.23 ±0.07 | 0.86 ±0.03 | 5.5 +2.1 −1.4 |

The test results set forth in Table II show that the pore-blocking procedure of the present invention affects the ultrafiltration rates, retention and separation factor of the membrane. Ultrafiltration rates decreased from 15% to 48%, mean retention of bovine serum albumin and gamma globulin (7S) increased from 0.09 to 0.23 and from 0.54 to 0.86, respectively, and the mean separation factor increased from 2.0 to 5.5. Also, the order of the ultrafiltration of the two test species had no appreciable effect upon the retention values obtained nor upon the separation factor. Furthermore, the value obtained for $dR_2/dR_1$ was calculated to be 2.3, or 4.6 times larger than the reciprocal of the mean separation factor of the unmodified membranes, thereby clearly satisfying the criterion for increased separation selectivity.

What is claimed is:

1. A method of modifying the pore size distribution of a microporous separation medium so as to provide it with a sharp upper cut-off of preselected molecular size, comprising the steps of:
   (a) filling the pores of said separation medium with a volatile liquid;
   (b) evaporating a controlled amount of said volatile liquid from said separation medium so as to lower the level of said liquid within said pores to below the bulk surface of said separation medium and thereby form voids at the entrances to said pores;
   (c) applying to said bulk surface of said separation medium a concentrated solution of a pore-blocking agent, said pore-blocking agent being a material which is insoluble in said volatile liquid and capable of being insolubilized in said solution and whose molecular size distribution has a lower limit corresponding to said preselected molecular size, whereby said pore-blocking agent selectively enters only those pores larger than said preselected size and remains in said voids at the entrances to said pores;

(d) removing excess pore-blocking agent solution from said bulk surface of said separation medium; and (e) insolubilizing said pore-blocking agent so as to immobilize it within said voids and thereby obstruct the entrances to all said pores larger than said preselected size.

2. The method of claim 1, wherein said pore-blocking agent is a polymerizable or cross-linkable material, and said insolubilizing step is effected by polymerization or cross-linking of said pore-blocking agent within said voids.

3. The method of claim 2, wherein said insolubilizing step is effected by applying to said bulk-surface of said separation medium a polymerization or cross-linking agent for said pore-blocking agent, and allowing said polymerization or cross-linking agent to soak into said pores into contact with said pore-blocking agent.

4. The method of claim 2, wherein said pore-blocking agent is a substantially monodisperse material.

5. The method of claim 2, wherein said pore-blocking agent is a cross-linkable protein or enzyme.

6. The method of claim 2, wherein said pore-blocking agent is a polymeric material.

7. The method of claim 1, wherein said separation medium is a polymeric membrane.

8. The method of claim 1, wherein said separation medium is a chromatographic gel.

* * * * *